US00PP33537P3

(12) United States Plant Patent
Scheffers

(10) Patent No.: US PP33,537 P3
(45) Date of Patent: Oct. 5, 2021

(54) ***TRADESCANTIA* PLANT NAMED 'DRATRA01'**

(50) Latin Name: *Tradescantia spathacea*
Varietal Denomination: DRATRA01

(71) Applicant: Dragontree Beheer B.V., Honselersdijk (NL)

(72) Inventor: Ruud Scheffers, Honselersdijk (NL)

(73) Assignee: Dragontree Beheer B.V., Honselersdijk (NL)

( * ) Notice: Subject to any disclaimer, the term of this patent is extended or adjusted under 35 U.S.C. 154(b) by 0 days.

(21) Appl. No.: 17/167,871

(22) Filed: Feb. 4, 2021

(65) Prior Publication Data

US 2021/0243930 P1 Aug. 5, 2021

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Tradescantia* plant named 'DRATRA01' which is characterized by glossy ovate foliage born on glossy greyed-purple stems, foliage with a dark-green adaxial surface and a dark purple abaxial surface, and the stability of these characteristics from generation to generation.

3 Drawing Sheets

Latin name of the genus and species: The Latin name of the genus and species of the novel variety disclosed herein is *Tradescantia spathacea.*

Variety denomination: The inventive cultivar of *Tradescantia* disclosed herein has been given the variety denomination 'DRATRA01'.

CROSS REFERENCE TO RELATED APPLICATIONS

This application claims priority to the Community Plant Variety Rights application number 2020/0361, filed Feb. 4, 2020, which is herein incorporated by reference.

BACKGROUND OF THE INVENTION

Parentage: 'DRATRA01' is a naturally-occurring branch mutation of an unnamed *Tradescantia spathacea* plant (not patented) which was discovered at a commercial greenhouse in Honselersdijk, the Netherlands in May of 2019. The mutation was initially noted to exhibit shorter and broader, ovate foliage with a dark green upper surface and a dark purple lower surface. The mutated branch was harvested from the parent plant, rooted, and grown to a mature size for further evaluation to confirm the uniformity and stability of the unique characteristics first observed. Upon confirmation of the stability and uniformity of the characteristics, the new plant was selected for commercialization.

Asexual Reproduction: Asexual reproduction of 'DRATRA01' is accomplished by way of rooting stem cuttings. Propagation was first performed in May of 2019 at the inventor's commercial greenhouse in Honselersdijk, the Netherlands. Through five subsequent generations, the unique features of this cultivar have proven to be stable and true to type.

SUMMARY OF THE INVENTION

The cultivar 'DRATRA01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DRATRA01'. These characteristics in combination distinguish 'DRATRA01' as a new and distinct *Tradescantia spathacea* cultivar:

1. *Tradescantia* 'DRATRA01' exhibits short and broad ovate foliage born on glossy dark greyed-purple stems; and
2. *Tradescantia* 'DRATRA01' exhibits foliage with a glossy, dark green adaxial surface; and
3. *Tradescantia* 'DRATRA01' exhibits foliage with a glossy, dark purple abaxial surface.

BOTANICAL DESCRIPTION OF THE PLANT

Figure 1:
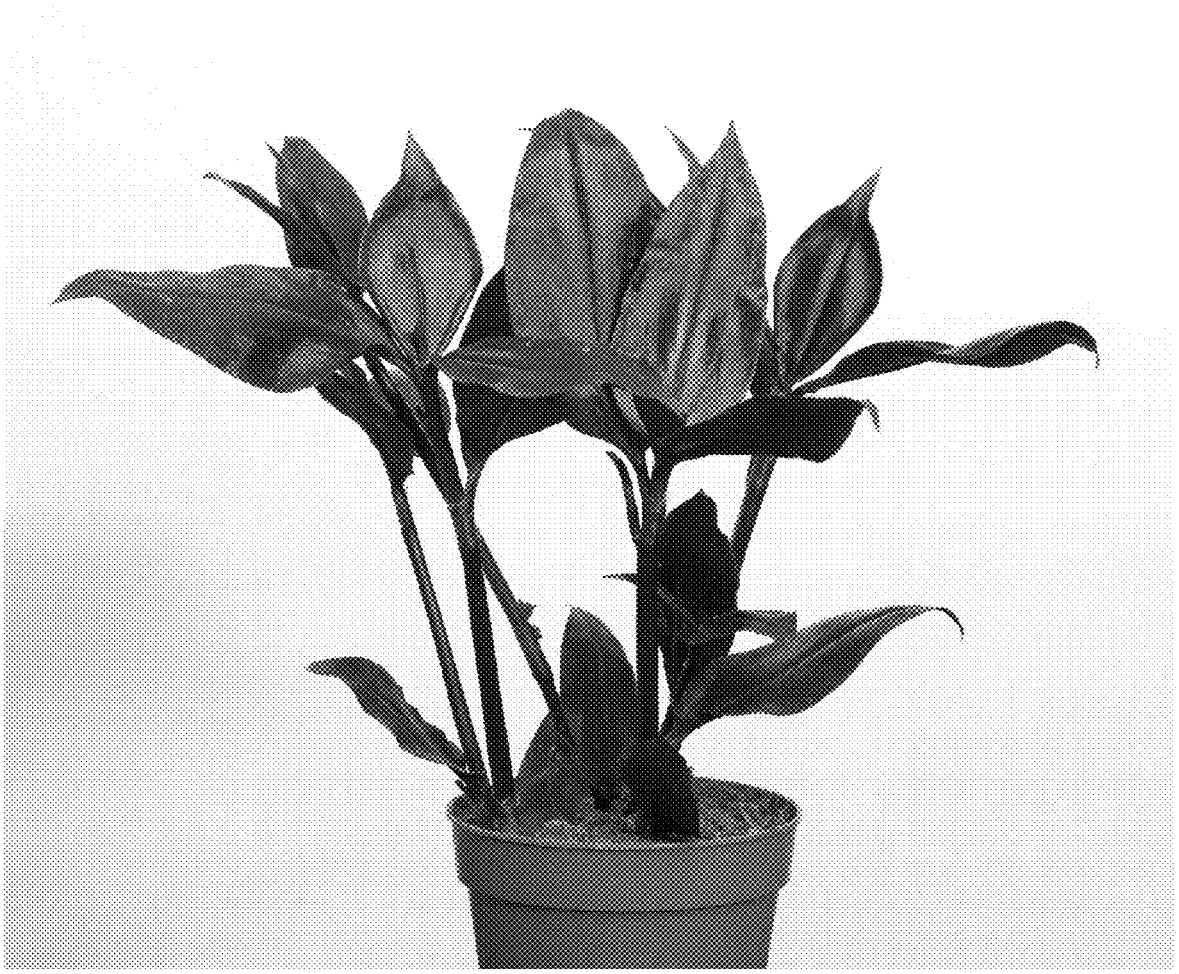
FIG. 1 illustrates, as nearly true as it is reasonably possible to make the same in color photographs of this type, an exemplary plant of 'DRATRA01' grown in Honselersdijk, the Netherlands. This plant, grown in a 11 cm nursery container, is approximately 12 months old from a rooted young plant.
Figure 2:
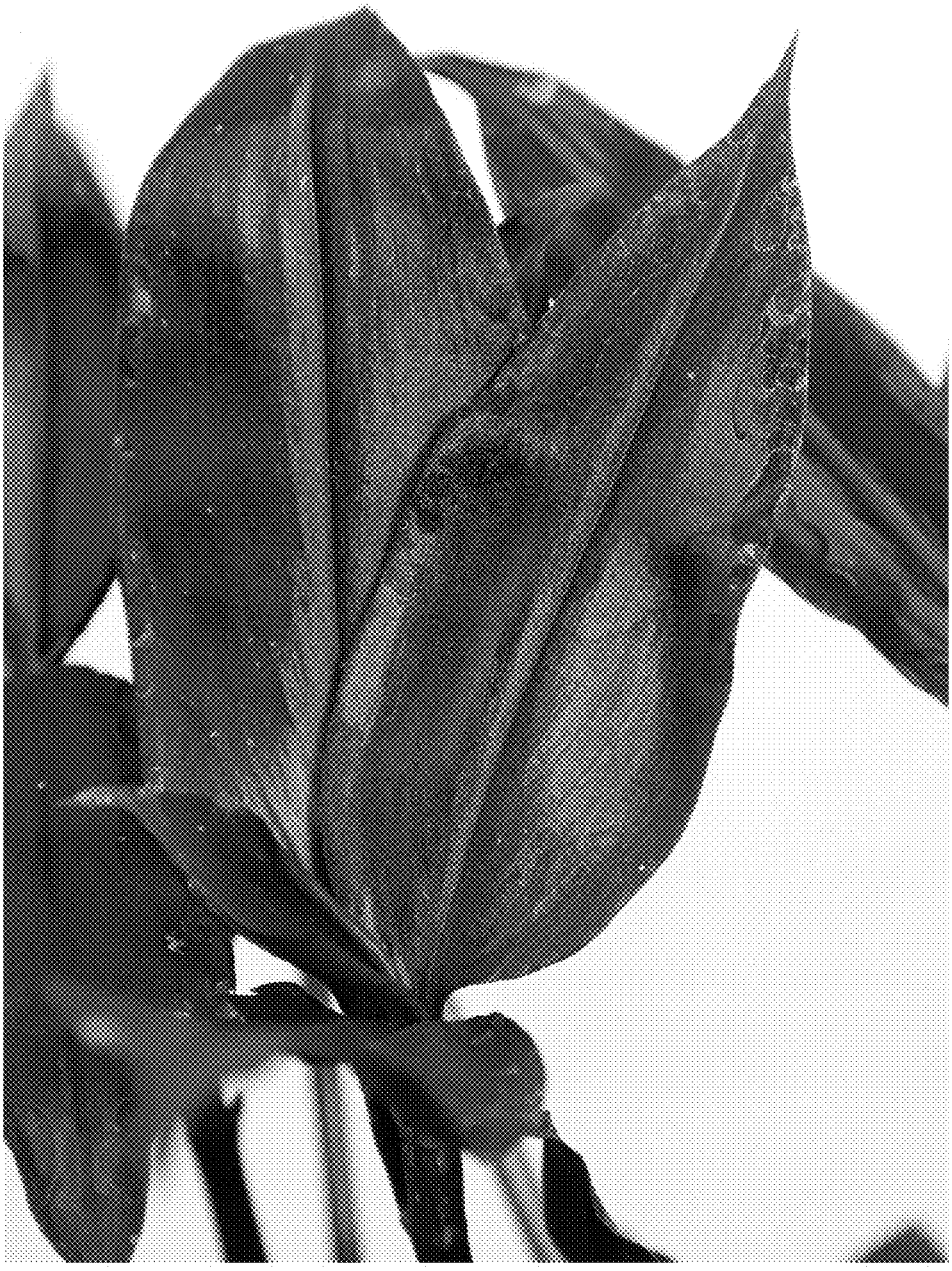
FIG. 2 illustrates, as nearly true as it is reasonably possible to make the same in color photographs of this type, the typical adaxial foliar surface of 'DRATRA01'.
Figure 3:
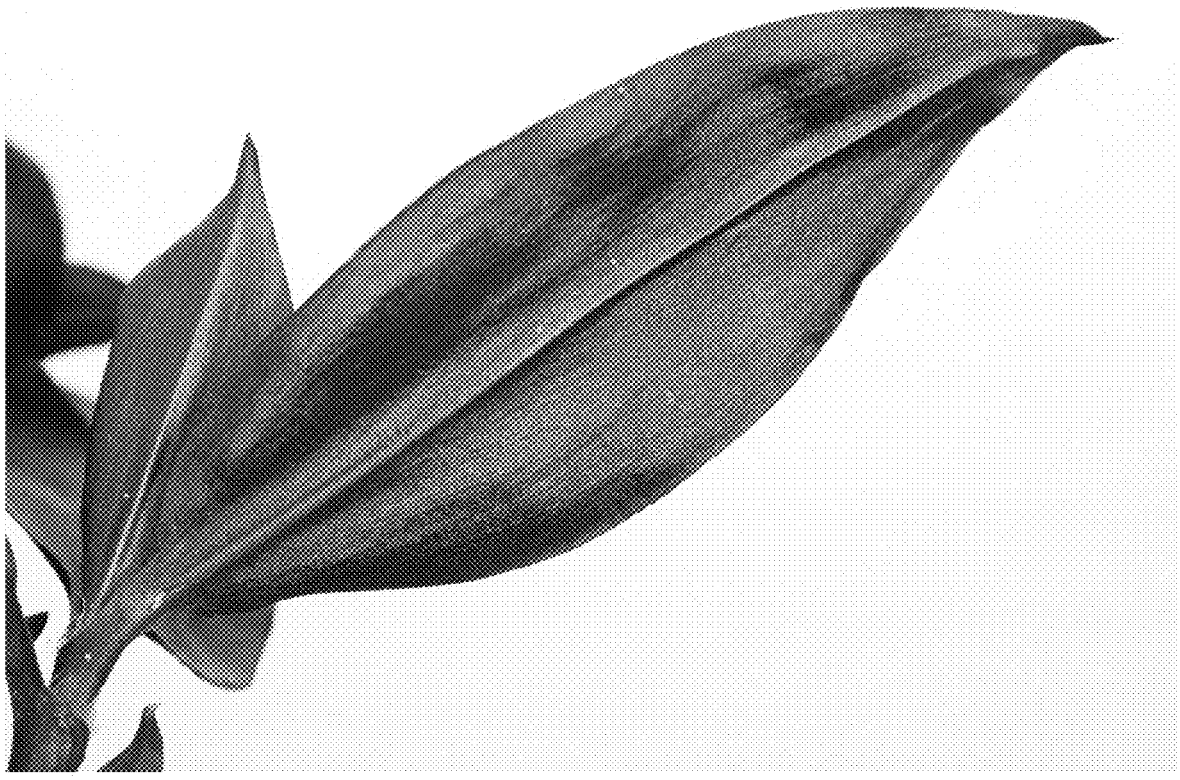
FIG. 3 illustrates, as nearly true as it is reasonably possible to make the same in color photographs of this type, the typical abaxial foliar surface foliage of 'DRATRA01'.

The following observations and measurements, made in November of 2020, describe averages from a sample set of six specimens of 12-month-old 'DRATRA01' plants in 11 cm nursery pots, with 3 rooted cuttings per pot, grown in Honselersdijk, the Netherlands. Plants were produced using conventional greenhouse production protocols for *Tradescantia* sp. which consisted of growing under shade, regular overhead irrigation and regular fertigation, and chemical control of thrips insects. No photoperiodic treatments or artificial light was given to the plants.

Those skilled in the art will appreciate that certain characteristics will vary with older or, conversely, with younger plants. 'DRATRA01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'DRATRA01' and comparisons with the parent plant and most similar commercial *Tradescantia* cultivar known to the inventor are provided below.

Plant description:

*Growth habit*.—Broad, upright herbaceous perennial.

*Plant profile*.—Broad ovate to broad obovate.

*Height*.—23.9 cm.

*Width*.—Average of 19.4 cm.

*Growth rate*.—Moderately fast growing.

*Plant vigor*.—Moderately to highly vigorous.

*Propagation*.—Method — Asexual propagation is accomplished by stem cuttings. Time to initiate roots — Approximately 30 days are required to initiate roots at 20 degrees Celsius.

*Time to produce a marketable* 12 *cm potted plant*.—Approximately 12 to 16 weeks. Pinching will increase lateral branching.

*Disease and pest resistance or susceptibility*.—Neither tolerance nor resistance to normal diseases and pests of *Tradescantia spathacea* have been observed.

*Environmental tolerances*.—Adapt to USDA Hardiness Zones 10 through 13 and temperatures as high as 40 degrees Celsius; moderate tolerance to rain and low to moderate tolerance to wind.

Root system:

*General*.—Slightly fibrous and non-fleshy; moderately branched and moderately dense rooting.

*Distribution in the soil profile*.—Moderately deep.

*Diameter*.—0.1 cm, on average.

*Texture*.—Densely covered with very short root hairs.

*Color*.—Greyed-white, nearest to RHS 156C.

Stems:

*Branching characteristics*.—Basally branched, with two main stems as observed. Main stems occasionally with lateral branches.

*Attitude*.—Upright; approximately 22.5 degrees from vertical.

*Main stems*.—Quantity — 2 per plant; 6 as observed in an 11 cm pot with 3 rooted cuttings per pot. Length — 16.2 cm. Diameter — 0.6 cm. Internode length — 1.4 cm with leaves mostly placed on the distal portion of the stem. Color, developing stem — Greyed-purple, nearest to RHS N186C yet slightly darker. Color, mature stem — Nearest to in between greyed-purple and brown, RHS N186C and 200B, and suffused with yellow-green, nearest to RHS 148A yet slightly darker. Color at the internodes — Greyed-purple, nearest to RHS N186C. Oldest wood — Brown, nearest to RHS 200A.

*Lateral branches*.—Quantity — 1 per plant, on average; 2 as observed in an 11 cm pot with 3 rooted cuttings per pot. Strength — Strong. Aspect — Rounded. Stem texture — Glabrous; smooth. Stem luster — Glossy. Color, developing branches — Greyed-purple, nearest to RHS N186C yet slightly darker. Color, mature branches — Nearest to in between greyed-purple and brown, RHS N186C and 200B, and suffused with yellow-green, nearest to RHS 148A yet slightly darker. Color at the internodes — Greyed-purple, nearest to RHS N186C.

Foliage:

*Arrangement*.—Alternate.

*Attachment*.—Sessile.

*Division*.—Simple.

*Attitude*.—Foliage near the apex is held upright to outward and becomes progressively more relaxed towards the base.

*Number of leaves per main stem*.—6.

*Lamina*.—Dimensions — 12.9 cm long and 4.8 cm wide. Shape — Ovate. Aspect — Very slightly carinate. Apex — Apiculate. Base — Attenuate; ligulate. Ligule — Type — Ciliate. Cilia — Length — 0.3 cm. Color — Greyed-yellow, nearest to a mixture of RHS 161B and 161C. Length — 1.3 cm. Width — 0.6 cm. Color — Greyed-red, nearest to RHS 182B. Veined greyed-purple, nearest to RHS 183A. Margin — Entire; coarsely undulate. Texture and luster of adaxial surface — Smooth, velutinous, and glossy. Texture and luster of abaxial surface — Smooth, slightly velutinous, and glossy. Color — Juvenile foliage, adaxial surface — Yellow-green, nearest to RHS 147A. Juvenile foliage, abaxial surface — Nearest to in between purple and greyed-purple; RHS N79A and N186C, yet closer to RHS N79A. Leaf tip is yellow-green, nearest to RHS 146A. Mature foliage, adaxial surface — Nearest to in between green and greyed-green; RHS 139A and N189A, yet closer to N189A. Mature foliage, abaxial surface — Purple; nearest to RHS N79A yet slightly darker. Leaf tip is yellow-green, nearest to RHS 147A. Venation — Pattern — Parallel. Color, adaxial surface — Nearest to in between green and greyed-green; RHS 139A and N189A, yet closer to N189A. Color, abaxial surface — Nearest to a mixture of green and yellow-green, RHS 143A and 144B.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

COMPARISONS WITH THE PARENT PLANT

Plants of the new cultivar 'DRATRA01' may be distinguished from the parent, an unnamed *Tradescantia spathacea* plant (not patented), by the characteristics described in Table 1.

TABLE 1

| Characteristic | 'DRATRA01' | The parent. |
|---|---|---|
| Foliage size. | Smaller than the parent. | Larger than 'DRATRA01'. |
| General coloration of the mature adaxial foliar surface. | A darker shade of green relative to the parent. | Lighter shade of green relative to 'DRATRA01'. |
| Leaf shape. | Ovate. | Lanceolate. |

Plants of the new cultivar 'DRATRA01' may be distinguished from the closest known commercial comparator, *Tradescantia spathacea* 'Satira Gold' (U.S. Plant Pat. No. 20,917), by the characteristics described in Table 2.

TABLE 2

| Characteristic | 'DRATRA01' | 'Satira Gold' |
|---|---|---|
| Growth habit. | More upright than 'Satira Gold'. | More compact than 'DRATRA01'. |

TABLE 2-continued

| Characteristic | 'DRATRA01' | 'Satira Gold' |
|---|---|---|
| Plant profile. | Broad ovate to broad obovate. | Globular. |
| Foliage shape. | Ovate. | Broad linear. |
| Foliage length. | Shorter than 'Satira Gold'. | Longer than 'DRATRA01'. |
| General coloration of the mature adaxial foliar surface. | in between green and greyed-green, generally appearing as a dark green coloration. | Light yellow-green with darker green longitudinal striping. |
| General coloration of the mature abaxial foliar surface. | Dark purple. | Light greyed-purple with violet longitudinal striping. |

That which is claimed is:

1. A new and distinct cultivar of *Tradescantia* plant named 'DRATRA01', substantially as described and illustrated herein.

* * * * *